United States Patent [19]

Zaiger

[11] Plant 4,155

[45] Nov. 22, 1977

[54] NECTARINE TREE

[76] Inventor: Chris Floyd Zaiger, 537 Rosemore Ave., Modesto, Calif. 95351

[21] Appl. No.: 731,557

[22] Filed: Oct. 12, 1976

[51] Int. Cl.[2] ..... A01H 5/03

[52] U.S. Cl. ..... Plt./41

[58] Field of Search ..... Plt./41

*Primary Examiner*—Robert E. Bagwill

[57] ABSTRACT

A new and distinct variety of nectarine tree principally characterized by its dwarf size, short leaf nodes, short heavy branches, and is a regular bearer of yellow-fleshed, clingstone fruit of good eating quality.

1 Drawing Figure

ORIGIN OF VARIETY

The new variety of dwarf nectarine tree was originated by me in my experimental orchard near Modesto, Calif.; as a second generation seedling from a cross between Red Grand Nectarine (U.S. Plant Pat. No. 1,060) and a seedling of Flory dwarf peach (unpatented).

ASEXUAL REPRODUCTION OF THE VARIETY

Asexual reproduction of the variety was accomplished by me in my experimental orchard by budding and shows that said characteristics come true to form and are established and transmitted through succeeding propagations.

SUMMARY OF THE VARIETY

My present discovery relates to a distinct variety of dwarf nectarine tree which is a regular and productive bearer of medium size, yellow flesh, clingstone fruit of good eating quality. The variety is further characterized by having the ornamental value of close leaf nodes and large showy flowers. Pruning, thinning and harvesting operations could be conducted without the use of ladders and by a person standing on the ground adjacent to the tree.

PHOTOGRAPHS OF VARIETY

The accompanying photographs show typical specimens of the foliage and fruit of my new variety with upper and lower surfaces of the foliage being illustrated and exterior and a sectional view of the fruit being shown. The colors are nearly true as is reasonably possible in a color representation of this type.

DESCRIPTION OF THE VARIETY

The following is a detailed description of the foliage and fruit of my new variety as based upon observations of specimens grown at Modesto, Calif., with color terminology in accordance with Reinhold Color Atlas by A. Kornerup and J. H. Wanscher.

TREE

Size: Dwarf. Average height 6 to 7 feet.
Vigor: Non vigorous.
Form: Spreading.
Density: Dense.
Production: Productive.
Bearing: Regular.

TRUNK

Size: Stocky.

Surface: Medium to shaggy.

BRANCHES

Size: Stocky.

LEAVES

Size: Large. Average length 6 inches.
Margin: Crenate.
Petiole: Short. Medium thickness.
Glands: Globose; average number and position — two to six; located on petiole or lower portion of leaf blade.
Color: Upper surface — Dark green (28-F-5) to grayish green (28-E-5).

FLOWER BUDS

Size: Large.
Length: Medium.

FLOWERS

Size: Large, showy.
Color: Pink.
Pollen: Present.
Blooming period: Feb. 24, 1976 to Mar. 10, 1976.

FRUIT

Maturity:
*Date of first picking.*—July 24, 1976.
*Date of last picking.*—July 29, 1976.
Size: Medium. Average diameter axially $2\frac{3}{8}''$. Average transversely in suture plane $2\frac{3}{8}''$.
Form: Uniform. Nearly globose.
Suture: Shallow — extends from base to apex.
Cavity: Slightly elongated in the suture plane, with suture showing on both sides.
*Average depth.*—$\frac{1}{4}''$.
*Average breadth.*—$\frac{3}{8}''$.
Apex: Short.

SKIN

Thickness: Thick to medium.
Texture: Tough. Smooth.
Tendency to crack: None.
Down: Wanting.
Color: Yellow ground color (4-A-8) to (5-A-7) overspread with red (9-A-8 to 9-B-8).

FLESH

Juice: Moderate.
Flavor: Subacid.
Ripens: Evenly.
Eating quality: Good.

Color: From cadmium yellow (4-A-8) to golden yellow (5-A-7).

STONE

Type: Clingstone.
Size: Medium. Average length $1\frac{1}{8}''$. Average breadth $\frac{7}{8}''$. Average thickness $\frac{5}{8}''$.
Form: Ovoid.
Sides: Equal.
Base: Mostly straight.
Surface: Pitted throughout.
Ridges: Rounded.
Tendency to split: None.
Color: Light brown (8-C-6).

USE

Home and local market.

KEEPING QUALITY

Medium.

SHIPPING QUALITY

Fair, not firm enough for commercial long distance shipment.

The tree and its fruit herein described may vary in slight detail due to climatic and soil conditions under which the variety may be grown; the present description being of the variety as grown at Modesto, Stanislaus County, Calif.

The following is claimed:

1. A new and distinct variety of nectarine tree, characterized by its dwarf size and heavy production, bearing medium size, highly colored, clingstone fruit of good eating quality.

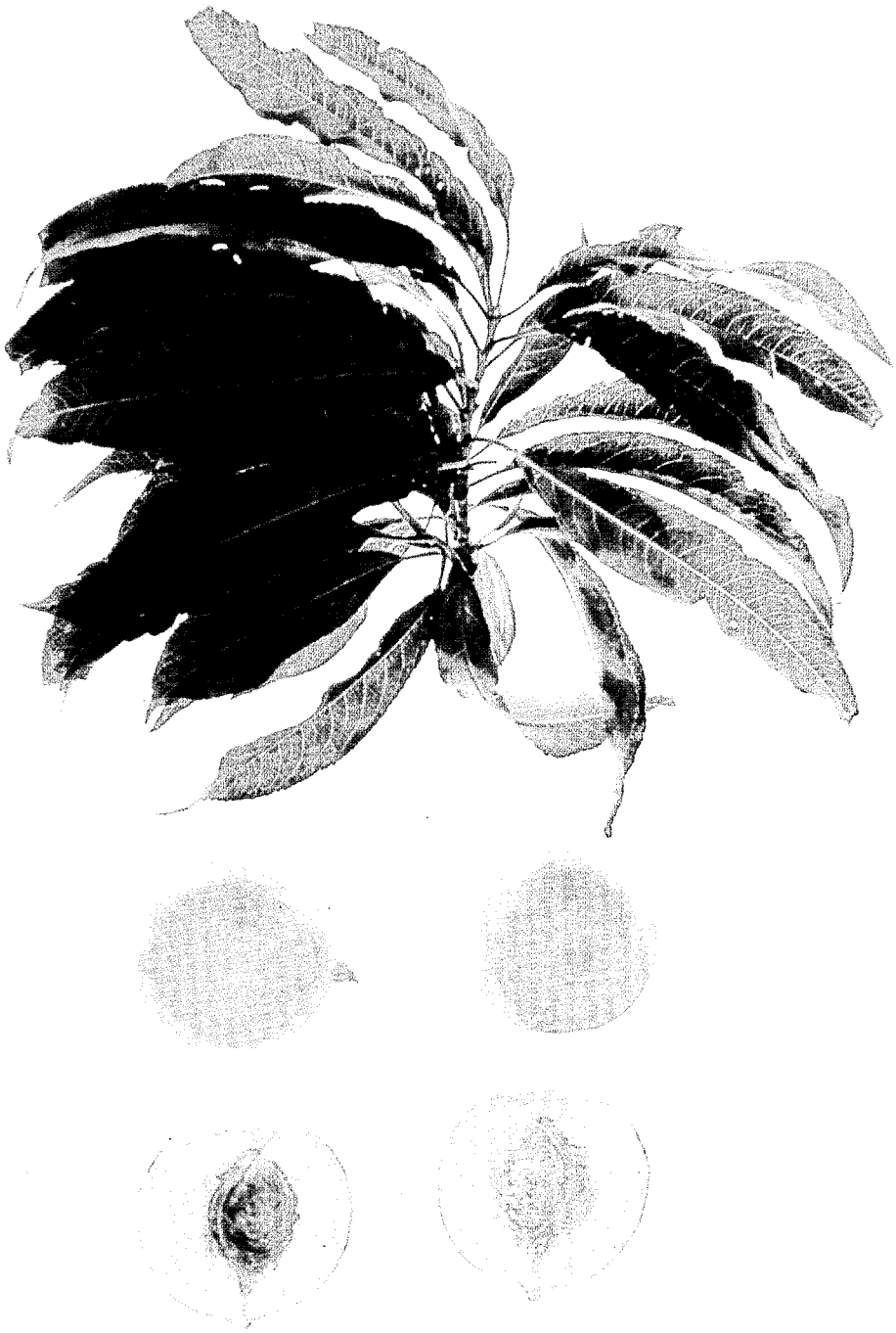

* * * * *